(12) United States Patent
Van Der Schaaf et al.

(10) Patent No.: US 6,306,987 B1
(45) Date of Patent: Oct. 23, 2001

(54) RUTHENIUM AND OSMIUM CATALYSTS

(75) Inventors: Paul Adriaan Van Der Schaaf, Allschwil; Andreas Hafner, Gelterkinden; Andreas Mühlebach, Frick, all of (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/446,052

(22) PCT Filed: Jun. 20, 1998

(86) PCT No.: PCT/EP98/03781

§ 371 Date: Dec. 16, 1999

§ 102(e) Date: Dec. 16, 1999

(87) PCT Pub. No.: WO99/00397

PCT Pub. Date: Jan. 7, 1999

(30) Foreign Application Priority Data

Jun. 27, 1997 (CH) .................................................... 1562/97

(51) Int. Cl.[7] .............................. C08F 4/80; C08F 32/00; C07F 15/00
(52) U.S. Cl. ........................ 526/171; 526/172; 526/281; 526/283; 526/308; 556/22; 556/136; 556/137; 502/155
(58) Field of Search ..................................... 526/171, 283, 526/308, 281, 172; 556/22, 136, 137; 502/155

(56) References Cited

FOREIGN PATENT DOCUMENTS

WO96/04289 * 2/1996 (WO) .
96/04289    2/1996 (WO) .

OTHER PUBLICATIONS

Harrity et al., Chromenes through metal–catalyzed reactions of styrenyl ethers, mechanism and utility in synthesis, J. Amer. Chem. Soc. v. 120, pp. 2343–2351, 1998.*

Tallarico et al., Ring–opening metathesis, a ruthenium catalyst caught in the act, J. Amer. Chem. Soc. v. 119, pp 7157–7158, 1997.*

J. Harrity et al., J. Am. Chem. Soc. (1998), 120(10), pp. 2343–2351.

B. Weber et al., J. Chem. Soc., Chem. Commun. (1994), (22), pp. 2595–2596.

* cited by examiner

Primary Examiner—David W. Wu
Assistant Examiner—R. Rabago
(74) Attorney, Agent, or Firm—Kevin T. Mansfield

(57) ABSTRACT

Disclosed is a compound of formula (I), and its use in preparing metathesis polymers of dicyclopentadiene and/or other strained cycloolefins

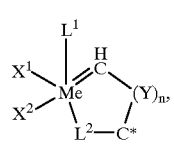

(I)

in which

Me is ruthenium or osmium;

$X^1$ and $X^2$ independently of one another are anionic ligands, or $X^1$ and $X^2$ together are a bis-anionic ligand;

Y is oxygen, sulfur or the groups —$NR^7$— or —$PR^7$—, where $R^7$ is hydrogen or a substituent selected from the group $C_1$–$C_6$alkyl, $C_6$–$C_{13}$aralkyl, sulfonyl and —$C(=O)R^{s2}$ and $R^{s2}$ is hydrogen or a substituent selected from the group $C_1$–$C_{12}$alkyl, $C_2$–$C_{12}$alkenyl, $C_3$–$C_{12}$cycloalkyl, $C_3$–$C_{12}$cycloalkenyl, $C_2$–$C_{11}$heterocycloalkyl, $C_2$–$C_{11}$heterocycloalkenyl, $C_5$–$C_{12}$aryl, $C_1$–$C_9$heteroaryl, $C_6$–$C_{14}$aralkyl, $C_2$–$C_{13}$heteroaralkyl, $C_6$–$C_{14}$aralkenyl and $C_3$–$C_{13}$heteroaralkenyl;

n is 0 or 1;

$L^1$ is tertiary phosphine;

and $L^2$ is a neutral $e^-$ donor ligand which is coordinated to the metal atom and is attached via the bridge group $C^*$ to the carbon atom of the carbene group if n is 0 and to Y if n is 1.

6 Claims, No Drawings

RUTHENIUM AND OSMIUM CATALYSTS

The invention relates to ruthenium and osmium carbene catalysts, to their preparation and to their use for synthesizing polymers, for ring-closing metathesis of olefins and for isomerizing olefins.

The thermal metathesis polymerization of cycloolefins which, are under ring strain, which has acquired great importance in recent times, requires appropriate catalysts. Whereas initially use was made of catalyst and cocatalyst—see, for example U.S. Pat. No. 4,060,468 and International Patent Application WO 93/13171—one-component catalysts have also been disclosed [H. H. Thoi et al, *J. Mol. Catal.* 15:245270 (1982)]. Catalysts of particular interest for the application are so-called metal carbenes, i.e. transition metal compounds, for example ruthenium and osmium complexes, having a group =CR*R** attached to the central metal atom [WO 93/20111; S. Kanaoka et al., *Macromolecules* 28:4707–4713 (1995); C. Fraseret al, *Polym. Prepr.* 36:237–238 (1995); P. Schwab et al., *Angew. Chem.* 107:2179–2181 (1995)]. This type of complex is also suitable for catalysing ring closure in dienes [WO 96104289]

The present invention is based on the object of providing further, improved catalysts for thermal metathesis polymerization.

It has surprisingly been found that ruthenium and osmium carbenes having $e^-$ donor ligands coordinated on the metal are excellent catalysts for metathesis reactions and for the ring closure of dienes. By an appropriate choice of these ligands it is possible to exercise close control over the reactivity, for example the latency, over a wide range. The bridged $e^-$ donor ligand is incorporated in the course of polymerization into the growing polymer and thereby removed from the metal centre, leading to an increased reactivity in comparison with catalysts already known.

The invention provides a compound of the formula

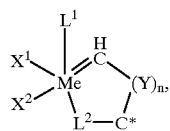

(I)

in which

Me is ruthenium or osmium;

$X^1$ and $X^2$ independently of one another are anionic ligands, or $X^1$ and $x^2$ together are a bis-anionic ligand;

Y is oxygen, sulfur or the groups —$NR^7$— or —PR—, where $R^7$ is hydrogen or a substituent from the group $C_1$–$C_6$alkyl, $C_6$–$C_{13}$aralkyl, sulfonyl and —C(=O)$R^{s2}$ and $R^{s2}$ is hydrogen or a substituent from the group $C_1$–$C_{12}$alkyl, $C_2$–$C_{12}$alkenyl, $C_3$–$C_{12}$cycloalkyl, $C_3$–$C_{12}$cycloalkenyl, $C_2$–$C_{11}$heterocycloalkyl, $C_2$–$C_{11}$ heterocycloalkenyl, $C_5$–$C_{12}$aryl, $C_1$–$C_9$heteroaryl, $C_6$–$C_{14}$aralkyl, $C_2$–$C_{13}$heteroaralkyl, $C_6$–$C_{14}$aralkenyl and $C_3$–$C_{13}$heteroaralkenyl;

n is 0 or 1;

$L^1$ is tertiary phosphine;

and $L^2$ is a neutral $e^-$ donor ligand which is coordinated to the metal atom and is attached via the bridge group C* to the carbon atom of the carbene group and to Y, and isomers of such compounds.

The invention likewise provides compounds of the formula I including all cases of isomerism of the type, for example, of coordination isomerism or bond isomerism, which results from differing spatial arrangement of the ligands around the central atom, but also stereoisomers.

In a particularly preferred embodiment of the invention Me is preferably ruthenium.

The terms and definitions used in the description of the present invention preferably have the following meanings:

The anionic ligands $X^1$ and $X^2$ are, for example, hydride ions ($H^-$) or are derived from inorganic or organic acids, examples being halides, e.g. $F^-$, $Cl^-$, $Br^-$ or $I^-$, fluoro complexes of the type $BF_4^-$, $PF_6^-$, $SbF_6^-$ or $AsF_6^-$, anions of oxygen acids, alcoholates or acetylides or anions of cyclopentadiene.

Anions of oxygen acids are, for example, sulfate, phosphate, perchlorate, perbromate, periodate, antimonate, arsenate, nitrate, carbonate, the anion of a $C_1$–$C_8$carboxylic acid, such as formate, acetate, propionate, butyrate, benzoate, phenylacetate, mono-, di- or trichloro- or -fluoroacetate, sulfonates, for example methylsulfonate, ethylsulfonate, propylsulfonate, butylsulfonate, trifluoromethylsulfonate (triflate), unsubstituted or $C_1$–$C_4$alkyl-, $C_1$–$C_4$alkoxy- or halo-, especially fluoro-, chloro- or bromo-substituted phenylsulfonate or benzylsulfonate, for example tosylate, mesylate, brosylate, p-methoxy- or pethoxyphenylsulfonate, pentafluorophenylsulfonate or 2,4,6-triisopropylsulfonate.

Such anions are, for example, anions of oxygen acids, examples being sulfate, phosphate, perchlorate, perbromate, periodate, antimonate, arsenate, nitrate or carbonate, sulfonates, for example methylsulfonate, ethyisulfonate, propylsulfonate, butylsulfonate, trifluoromethylsulfonate (triflate), unsubstituted or $C_1$–$C_4$alkyl-, $C_1$–$C_4$alkoxy- or halo-, especially fluoro-, chloro- or bromo-substituted phenylsulfonate or benzylsulfonate, for example tosylate, mesylate, brosylate, p-methoxy- or p-ethoxyphenylsulfonate, pentafluorophenylsulfonate or 2,4,6-triisopropylsulfonate, phosphonates, for example methylphosphonate, ethylphosphonate, propylphosphonate, butylphosphonate, phenylphosphonate, p-methylphenylphosphonate or benzylphosphonate, carboxylates derived from a $C_1$–$C_8$carboxylic acid, for example formate, acetate, propionate, butyrate, benzoate, phenylacetate, mono-, di- or trichloro- or -fluoroacetate, and also $C_1$–$C_{12}$—, preferably $C_1$–$C_6$—and, with particular preference, $C_1$–$C_4$alcoholates, which in particular are branched, being for example of the formula $R_xR_yR_zC$—O$^-$ in which $R_x$ is H or $C_1$–$C_{10}$alkyl, $R_y$ is $C_1$–$C_{10}$alkyl and $R_z$ is $C_1$–$C_{10}$alkyl or phenyl, and the sum of the carbon atoms of $R_x$, $R_y$ and $R_z$ is at least 2, preferably at least 3 and up to 10.

Other suitable anions are $C_3$–$C_x$—, preferably $C_5$–$C_{14}$—and, with particular preference, $C_5$–$C_{12}$acetylides, which are of the formula $R_w$—C≡C$^-$ in which $R_w$ is $C_1$–$C_{16}$alkyl, preferably α-branched $C_3$–$C_{12}$alkyl, for example of the formula $R_xR_yR_zC$—, or is unsubstituted or mono- to tri-$C_1$–$C_4$alkyl or —$C_1$–$C_4$alkoxy-substituted phenyl or benzyl. Some examples are i-propyl, i- and t-butyl, phenyl, benzyl, 2-methylphenyl, 2,6-dimethylphenyl, 2-i-propylphenyl, 2-i-propyl-6-methylphenyl, 2-t-butylphenyl, 2,6-di-t-butylphenyl and 2-methyl-6-t-butylphenyl acetylide.

Further anionic ligands are organic radicals having negative charges, such as $C_1$–$C_{12}$alkyl, e.g. methyl, or aralkyl, e.g. benzyl Particularly preferred anionic ligands $X^1$ and $X^2$ are $H^-$, $F^-$, $Cl^-$, $Br^-$, $BF_4^-$, $PF_6^-$, $SbF_6^-$, $AsF_6^-$, $CF_3SO_3^-$, $C_6H_5$—

$O_3^-$, 4-methyl-$C_6H_4$—$SO_3^-$, 3,5-dimethyl-$C_6H_3$—$SO_3^-$, 2,4,6-trimethyl-$C_6H_2$—$SO_3^-$ and 4-$CF_3$13 $C_6H_4$—$SO_3^-$ and also cyclopentadienyl (Cp$^-$). Cl$^-$ is particularly preferred.

Examples of bisanionic ligands X, X', Y and Y' are the bisanions of diols, diamines and hydroxyamines, such as catechol, N,N'-dimethyl-1,2-benzenediamine, 2-(methylamino)phenol, 3-(methylamino)-2-butanol and N,N'-bis(1,1-dimethylethyl)-1,2-ethanediamine.

Tertiary-substituted phosphine $L^1$ contains 3–about 40, preferably 3–30 and, with particular preference, 3–18 carbon atoms. The tertiary-substituted phosphine is preferably a compound of the formula

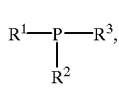

(II)

in which $R^1$, $R^2$ and $R^3$ independently of one another are $C_1$–$C_{20}$alkyl, $C_3$–$C_{12}$cycloalkyl, $C_2$–$C_{11}$heterocycloalkyl, $C_5$–$C_{12}$aryl, $C_1$–$C_{12}$heteroaryl or $C_6$–$C_{14}$aralkyl, where alkyl, cycloalkyl, heterocycloalkyl, aryl, heteroaryl and aralkyl are unsubstituted or substituted by one or more substituents of the group consisting of $C_1$–$C_6$alkyl, $C_1$–$C_6$alkoxy, $C_1$–$C_6$haloalkyl, $C_5$–$C_{12}$aryl, —$NO_2$, $SO_3^-$, ammonium and halogen; the radicals $R^1$ and $R^2$ together are unsubstituted or $C_1$–$C_6$alkyl-, $C_1$–$C_6$haloalkyl-, —$NO_2$— or $C_1$–$C_6$alkoxy-substituted tetra- or pentamethylene, which may be fused to 1 or 2 1,2-phenylene radicals, and $R^3$ is as defined above.

Examples of alkyl are methyl, ethyl and the isomers of propyl, butyl, pentyl, hexyl, heptyl, octyl, nonyl, decyl, undecyl and dodecyl. An example of aryl-substituted alkyl is benzyl. Examples of alkoxy are methoxy, ethoxy and the isomers of propoxy and butoxy.

Some examples of cycloalkyl are cyclobutyl, cycloheptyl, cyclooctyl and especially cyclopentyl and cyclohexyl. Examples of substituted cycloalkyl are methyl-, dimethyl-, trimethyl-, methoxy-, dimethoxy-, trimethoxy-, trifluoromethyl-, bis-trifluoromethyl- and tris-trifluoromethyl-substituted cyclopentyl and cyclohexyl.

Examples of aryl are phenyl and naphthyl. Examples of aryloxy are phenoxy and naphthyloxy. Examples of substituted aryl are methyl-, dimethyl-, trimethyl-, methoxy-, dimethoxy-, trimethoxy-, trifluoromethyl-, bis-trifluoromethyl- or tris-trifluoromethyl-substituted phenyl. An example of aralkyl is benzyl. Examples of substituted aralkyl are methyl-, dimethyl-, trimethyl-, methoxy-, dimethoxy-, trimethoxy-, trifluoromethyl-, bis-trifluoromethyl or tris-trifluoromethyl-substituted benzyl.

In the context of the present invention's description heterocycloalkyl embraces one or two and heteroaryl from one to four heteroatoms, the heteroatoms being selected from the group nitrogen, sulfur and oxygen. Some examples of heterocycloalkyl are tetrahydrofuryl, pyrrolidinyl, piperazinyl and tetrahydrothienyl. Some examples of heteroaryl are furyl, thienyl, pyrrolyl, pyridyl and pyrimidinyl.

Preference is given to tertiary-substituted phosphine (II) in which $R^1$, $R^2$ and $R^3$ are identical substituents, e.g. $C_1$–$C_6$alkyl or phenyl. Particular preference is given, furthermore, to radicals $R^1$, $R^2$ and $R^3$ which are sterically bulky, for example cyclic or branched, especially α,α-di-branched and very especially a-branched alkyl groups.

Another group of preferred compounds is formed by those compounds (I) in which $L^1$ is tertiary-substituted phosphine (II) in which $R^1$, $R^2$ and $R^3$ independently of one another are $C_1$–$C_{12}$alkyl, $C_5$–$C_8$cycloalkyl, $C_6$–$C_{12}$aryl or $C_7$–$C_{13}$aralkyl in which alkyl, cycloalkyl, aryl and aralkyl are unsubstituted or substituted by one or more substituents selected from the group $C_1$–$C_6$alkyl, $C_1$–$C_6$alkoxy, $C_1$–$C_6$haloalkyl, sulfo, trimethylamino, triethylamino, ammonium and trifluoromethyl.

Within this group particular preference is given to those phosphines (II) in which $R^1$, $R^2$ and $R^3$ independently of one another are $C_1$–$C_8$alkyl, $C_5$- or $C_6$-cycloalkyl, $C_6$–$C_{10}$aryl or $C_7$–$C_{12}$aralkyl in which alkyl, cycloalkyl, aryl and aralkyl are unsubstituted or substituted by from one to three substituents selected from the group methyl, methoxy, ethyl, ethoxy and trifluoromethyl.

Particular preference is given to phosphines (II) in which $R^1$, $R^2$ and $R^3$ are methyl, ethyl, n- or i-propyl, n-, i-, s- or t-butyl, 1-, 2- or 3-pentyl, 1-, 2-, 3- or 4-hexyl, cyclopentyl, cyclohexy phenyl, naphthyl or benzyl.

Particular preference is given to compounds (II) in which $R^1$, $R^2$ and $R^3$ are methyl, ethyl, n- or i-propyl, n-, i-, s- or t-butyl, 1-, 2- or 3-pentyl, 1-, 2-, 3- or 4-hexyl, cyclohexy phenyl, naphthyl or benzyl, e.g. (i-$C_3H_7$)$_3$P, ($C_5H_9$)$_3$P and ($C_6H_{11}$)$_3$P.

Suitable e$^-$ donor ligands are neutral and have electron donor properties. Such ligands are derived, for example, from unsubstituted or substituted heteroarenes from the group consisting of furan, thiophene, pyrrole, pyridine, bis-pyridine; picolylimine, γ-pyran, γ-thiopyran, phenanthroline, pyrimidine, bis-pyrimidine, pyrazine, indole, coumarone, thionaphthene, carbazole, dibenzofuran, dibenzothiophene, pyrazole, imidazole, benzimidazole, oxazole, thiazole, bis-thiazole, isoxazole, isothiazole, quinoline, bis-quinoline, isoquinoline, bis-isoquinoline, acridine, chromene, phenazine, phenoxazine, phenothiazine, triazine, thianthrene, purine, bis-imidazole and bis-oxazole.

Examples of substituents of these groups are OH, halo, —C(=O)—O$R_{s1}$, —O—C(=O)$R_{s4}$, C(=O)$R_{s2}$, nitro, $NH_2$, cyano, —$SO_3M_y$, —O—$SO_3M_y$, —N($R_{20}$)—$SO_3M_y$, —N=N—$R_{s2}$, $C_1$–$C_{12}$alkyl, $C_2$–$C_{12}$alkenyl, $C_1$–$C_{12}$alkoxy, $C_3$–$C_{12}$cycloalkyl, $C_3$–$C_{12}$cycloalkenyl, $C_2$–$C_{13}$heterocycloalkenyl, $C_2$–$C_{13}$heterocycloalkenyl, $C_5$–$C_{12}$aryl, $C_5$–$C_{12}$aryloxy, $C_6$–$C_{14}$aralkyl, $C_6$–$C_{14}$aralkoxy, $C_6$–$C_{14}$aralkenyl, $C_1$–$C_9$heteroaryl, $C_2$–$C_9$heteroaryloxy, $C_2$–$C_{12}$heteroaralkyl, $C_3$–$C_{12}$heteroaralkenyl, monoamino, diamino, sulfonyl, sulfonamide, carbamide, carbamate, sulfonhydrazide, carbohydrazide, carbohydroxamic acid and aminocarbonylamide, in which $M_y$, $R_{s1}$, $R_{s2}$, $R_{s4}$ and $R_{20}$ are $C_1$–$C_{12}$alkyl, $C_2$–$C_{12}$alkenyl, $C_3$–$C_{12}$cycloalkyl, $C_3$–$C_{12}$cycloalkenyl, $C_2$–$C_{13}$heterocycloalkyl, $C_2$–$C_{13}$heterocycloalkenyl, $C_5$–$C_{12}$aryl, $C_5$–$C_{14}$aralkyl, $C_6$–$C_{14}$aralkenyl, $C_1$–$C_9$heteroaryl, $C_2$–$C_{12}$heteroaralkyl or $C_3$–$C_{12}$heteroaralkenyl and $R_{s1}$, $R_{s2}$, $R^{s4}$ and $R_{20}$ are otherwise hydrogen, and alkyl, alkenyl, cycloalkyl, cycloalkenyl, heterocycloalkyl, heterocycloalkenyl, aryl, aralkyl, aralkenyl, heteroaryl, heteroaralkyl or heteroaralkenyl are in turn unsubstituted or substituted by one of the specified substituents; and y is 1 and M is a monovalent metal or y is 1/2 and M is a bivalent metal cation.

In the context of the description of the present invention the term metal cations means alkali metal cations, for example Li, Na or K, alkaline earth metal, for example Mg, Ca or Sr, or Mn, Fe, Zn or Ag cations. Salts with lithium, sodium and potassium cations are preferred.

Monoamino, diamino, carbamide, carbamate, carbohydrazide, sulfonamide, sulfohydrazide and aminocarbonylamide correspond preferably to a group $R_8C(=O)$(NH)$_p$N($R_9$)—, —C(=O)(NH)$_p$N$R_8R_9$, $R_8$O —C(=O)(NH)$_p$N($R_9$)—, $R_8R_{40}$N—C(=O)(NH)$_p$N($R_9$)—, —OC (=O)(NH)$_p$NR$_8$R$_9$, —N(R$_{40}$)—C(=O)(NH)pNR$_8$R$_9$, R$_8$S(O)$_2$(NH)$_p$N(R$_9$)—; —S(O)$_2$(NH)$_p$NR$_8$R$_9$; R$_8$R$_{40}$NS(O)$_2$N(R$_9$)— or —NR$_{40}$S(O)$_2$NR$_8$R$_9$, in which R$_8$, R$_9$ and R$_{40}$ independent of one another are hydrogen or substituents from the group OH, C$_1$–C$_{12}$alkyl, C$_2$–C$_{12}$alkenyl, C$_3$–C$_{12}$cycloalkyl, C$_3$–C$_{12}$cycloalkenyl, C$_2$–C$_{13}$heterocycloalkyl, C$_2$–C$_{13}$heterocycloalkenyl, C$_5$–C$_{12}$aryl, C$_1$–C$_9$heteroaryl, C$_6$–C$_{14}$aralkyl, C$_7$–C$_{14}$aralkenyl with C$_2$–C$_6$alkenylene and C$_5$–C$_{12}$aryl, C$_6$–C$_{15}$heteroarayl, C$_5$–C$_{14}$heteroaralkenyl and di-C$_6$–C$_{10}$aryl-C$_1$–C$_6$alkyl, and in which in the group R$_8$R$_9$N the substituents R$_{8'}$ and R$_{9'}$ independently of one another are hydrogen or substituents from the group OH, SO$_3$M$_y$, OSO$_3$M$_y$, C$_1$–C$_{12}$alkyl, C$_3$–C$_{12}$cycloalkyl, C$_2$–C$_{11}$heterocycloalkyl, C$_6$–C$_{10}$aryl, C$_5$–C$_9$heteroaryl, C$_7$–C$_{11}$aralkyl, C$_6$–C$_{10}$ heteroaralkyl, C$_8$–C$_{16}$aralkenyl with C$_2$–C$_6$-alkenylene and C$_6$–C$_{10}$aryl and di-C$_6$–C$_{10}$aryl-C$_1$–C$_6$alkyl, which are unsubstituted or substituted by one or more substituents from the group OH, halo, —C(=O)—OR$_{s1}$, —O—C(=O)R$_{s4}$, —C(=O)R$_{s2}$, nitro, NH$_2$, cyano, —SO$_3$M$_y$, —O—SO$_3$M$_y$, —N(R$_{20}$)—SO$_3$M$_y$, —N=N—R$_{s2}$, C$_1$–C$_{12}$alkyl, C$_2$–C$_{12}$alkenyl, C$_1$–C$_{12}$alkoxy, C$_3$–C$_{12}$cycloalkyl, C$_3$–C$_{12}$cycloalkenyl, C$_2$–C$_{13}$heterocycloalkyl, C$_2$–C$_{13}$-heterocycloalkenyl, C$_5$–C$_{12}$aryl, C$_5$–C$_{12}$aryloxy, C$_6$–C$_{14}$aralkyl, C$_6$–C$_{14}$aralkoxy, C$_7$–C$_{14}$aralkenyl, C$_1$–C$_9$heteroaryl, C$_2$–C$_9$heteroaryloxy, C$_2$–C$_{12}$heteroaralkyl, C$_3$–C$_{12}$heteroaralkenyl, monoamino, diamino, sulfonyl, sulfonamide, carbamide, carbamate, sulfohydrazide, carbohydrazide, the carbohydramic acid radical and aminocarbonylamide radical, in which M$_y$, R$_{s1}$, R$_{s2}$, R$_{s4}$ and R$_{20}$ are C$_1$–C$_{12}$alkyl, C$_2$–C$_{12}$alkenyl, C$_3$–C$_{12}$cycloalkyl, C$_3$–C$_{12}$cycloalkenyl, C$_2$–C$_{13}$-heterocycloalkyl, C$_2$–C$_{11}$heterocycloalkenyl, C$_6$–C$_{12}$aryl, C$_6$–C$_{13}$aralkyl C$_6$–C$_{13}$aralkenyl, C$_1$–C$_9$-heteroaryl, C$_2$–C$_{12}$heteroaralkyl or C$_3$–C$_{12}$heteroaralkenyl and R$_{s1}$, R$_{s2}$, R$_{s4}$ and R$_{20}$ are otherwise hydrogen, and alkyl, alkenyl, cycloalkyl, cycloalkenyl, heterocycloalkyl, heterocycloalkenyl, aryl, aralkyl, aralkenyl, heteroaryl, heteroaralkyl or heteroaralkenyl in turn are unsubstituted or substituted by one of the specified substituents; and y is 1 and M is a monovalent metal or y is 1/2 and M is a divalent metal; or R$_8$ and R$_9$ or R$_{8'}$ and R$_{9'}$ or R$_8$ and R$^{40}$ in the case of —NR$_8$R$_9$ or —NR$_8$·R$_{9'}$ or R$_8$R$_{40}$N— together are tetramethylene, pentamethylene, —(CH$_2$)$_2$——(CH$_2$)$_2$—, —(CH$_2$)$_2$—S—(CH$_2$)$_2$— or —(CH$_2$)$_2$—, and R$_7$ is hydrogen, C$_1$–C$_6$alkyl, C$_6$–C$_{13}$aralkyl, —C(=O)R$_{72}$ or sulfonyl.

The sulfonyl substituent corresponds, for example, to the formula R$_{10}$—SO$_2$— in which R$_{10}$ is C$_1$–C$_{12}$alkyl, C$_3$–C$_{12}$cycloalkyl, C$_2$–C$_{11}$heterocycloalkyl, C$_5$–C$_{12}$aryl, C$_1$–C$_9$heteroaryl, C$_6$–C$_{13}$aralkyl or C$_2$–C$_{13}$heteroaralkyl which is unsubstituted or substituted by one or more substituents from the group OH, halo, —C(=O)—OR$_{s1}$, —O—C(=O)R$_{s4}$, —C(=O)R$_{s2}$, nitro, NH$_2$, cyano, —SO$_3$M$_y$, —O—SO$_3$M$_y$, —N(R$_{20}$)—SO$_3$M$_y$, —N=N—R$_2$, C$_1$–C$_{12}$alkyl, C$_2$–C$_{12}$alkenyl, C$_1$–C$_{12}$alkoxy, C$_3$–C$_{12}$cycloalkyl, C$_3$–C$_{12}$cycloalkenyl, C$_2$–C$_{13}$heterocycloalkyl, C$_2$–C$_{13}$heterocycloalkenyl, C$_5$–C$_{12}$aryl, C$_5$–C$_{12}$aryloxy, C$_6$–C$_{13}$aralkyl, C$_6$–C$_{13}$aralkoxy, C$_6$–C$_{13}$aralkenyl, C$_1$–C$_9$heteroaryl, C$_2$–C$_9$heteroaryloxy, C$_2$–C$_{12}$heteroaralkyl, C$_3$–C$_{12}$heteroaralkenyl, monoamino, diamino, sulfonyl, sulfonamide, carbamide, carbamate, sulfohydrazide, carbohydrazide, the carbohydroxamic acid radical and aminocarbonylamide radical, in which M$_y$, R$_{s1}$, R$_{s2}$, R$_{s4}$ and R$_{20}$ are C$_1$–C$_{12}$alkyl, C$_2$–C$_{12}$alkenyl, C$_3$–C$_{12}$cycloalkyl, C$_3$–C$_{12}$cycloalkenyl, C$_2$–C$_{13}$-heterocycloalkyl, C$_2$–C$_{13}$heterocycloalkenyl, C$_5$–C$_{12}$aryl, C$_6$–C$_{13}$aralkyl, C$_6$–C$_{13}$aralkenyl, C$_1$–C$_9$heteroaryl, C$_2$–C$_{12}$heteroaralkyl or C$_3$–C$_{12}$heteroaralkenyl and R$_{s1}$, R$_{s2}$, R$_{s4}$ and R$_{20}$ are otherwise hydrogen, and alkyl, alkenyl, cycloalkyl, cycloalkenyl, heterocycloalkyl, heterocycloalkenyl, aryl, aralkyl, aralkenyl, heteroaryl, heteroaralkyl or heteroaralkenyl in turn are unsubstituted or substituted by one of the specified substituents; and y is 1 and M is a monovalent metal or y is 1/2 and M is a bivalent metal cation.

Preferred e$^-$ donor ligands L$^2$ are derived, for example, from heteroarenes of the group:

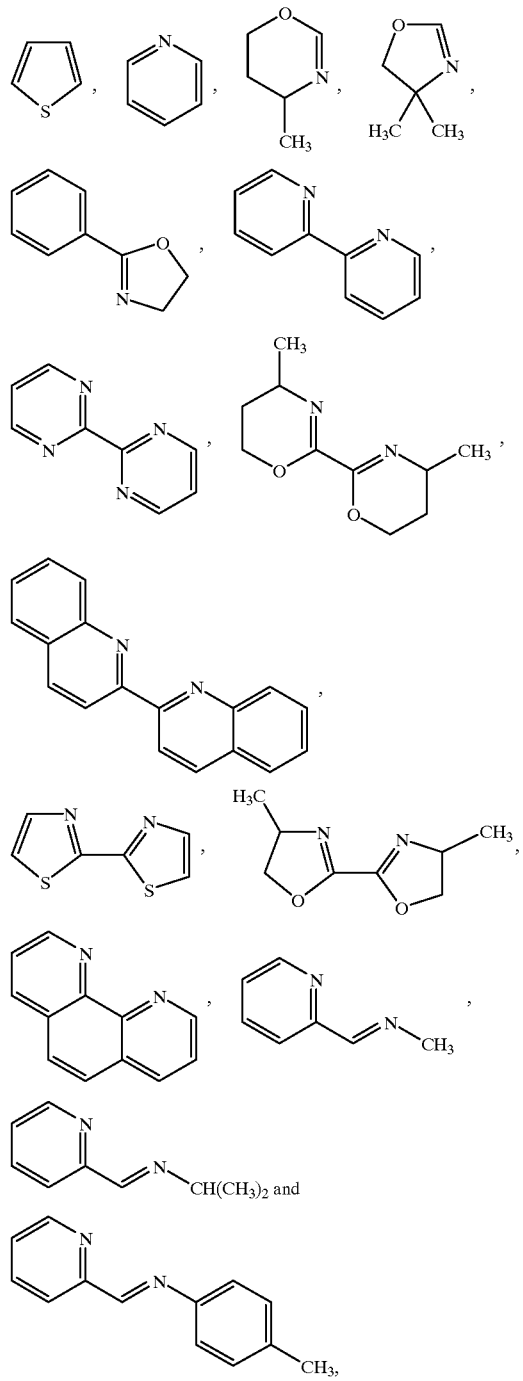

tertiary phosphines of the formula PR$^1$R$^2$R$^3$, amines of the formula NR$^1$R$^2$R$^3$, imines of the formula R$^1$—N=CR$^2$R$^3$, ketones of the formula —C(=O)R¹R², esters of the formula R²C(=O)OR¹, alcohols of the formula HOR¹, ethers of the formula R¹OR², thioethers of the formula R¹SR² or nitriles of the formula R¹CN, in which R¹, R² and R³ independently of one another are $C_1$–$C_{20}$alkyl, $C_3$–$C_{12}$cycloalkyl, $C_2$–$C_{11}$heterocycloalkyl, $C_5$–$C_{12}$aryl, $C_1$–$C_9$heteroaryl or $C_6$–$C_{16}$-aralkyl, where alkyl, cycloalkyl, heterocycloalkyl, aryl, heteroaryl and aralkyl are unsubstituted or substituted by one or more substituents selected from the group consisting of $C_1$–$C_6$alkyl, $C_1$–$C_6$alkoxy, $C_1$–$C_6$haloalkyl, $C_5$–$C_{16}$aryl, —$NO_2$, $SO_3^-$, ammonium and halogen; the radicals R¹ and R² together are unsubstituted or $C_1$–$C_6$alkyl-, $C_1$–$C_6$haloalkyl- , —$NO_2$—or $C_1$–$C_6$alkoxy-substituted tetra- or pentamethylene, or are unsubstituted or $C_1$–$C_6$alkyl-, $C_1$–$C_6$haloalkyl-, —$NO_2$—or $C_1$–$C_6$alkoxy-substituted tetra- or pentamethylene fused to 1 or 2 1,2-phenylenes, and R³ is as defined above.

A preferred group of compounds is formed by compounds (I) in which L² is pyridyl, a phosphine group, an amino group, alkoxy, aryloxy or an imino group, which are unsubstituted or substituted by one or more substituents from the group $C_1$–$C_{12}$alkyl, $C_2$–$C_{11}$heterocycloalkyl, $C_5$–$C_9$heteroaryl, monoamino and diamino. Examples thereof are $(CH_3)_2N$—, $H_3CO$—, $H_3CN=$,

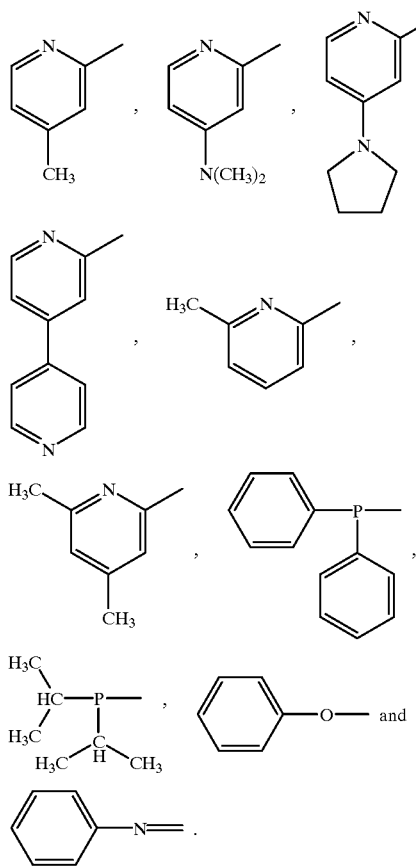

The bridge group C* which is attached to the carbon atom of the carbene group and to Y is, for example, $C_1$–$C_8$alkylene, $C_2$–$C_8$alkenylene, $C_2$–$C_8$alkynylene, $C_3$–$C_{12}$cycloalkylene, $C_6$–$C_{10}$arylene or $C_7$–$C_{12}$aralkylene, it being possible for alkylene, alkenylene, alkynylene, arylene and aralkylene to be interrupted by one or more bivalent groups selected from the group —O—, —S—, —C(=O)—, —C(=O)O—, —OC(=O)O—, —$SO_2$—, —$OSO_2$— and —R⁷N—, in which R⁷ is hydrogen or a substituent from the group OH, $SO_3M_y$, $OSO_3M_y$, $C_1$–$C_{12}$alkyl, $C_3$–$C_{12}$cycloalkyl, $C_2$–$C_{11}$heterocycloalkyl, $C_5$–$C_{10}$aryl, $C_1$–$C_9$heteroaryl, $C_6$–$C_{14}$aralkyl, $C_1$–$C_{10}$heteroaralkyl, $C_8$–$C_{16}$aralkenyl with $C_2$–$C_6$alkenylene and $C_5$–$C_{10}$aryl, di-$C_6$–$C_{10}$aryl-$C_1$–$C_6$alkyl, —C(=O)(NH)$_p$N(R⁸)—, —O—C(=O)(NH)$_p$N(R⁸)—, —N(R⁸)C(=O)(NH)$_p$NR⁹—,—$SO_2$(NH)$_p$N(R⁸)—, —NR⁸$SO_{20}$— and —N(R⁸)S(O)$_2$N(R⁹)—, in which R⁸ and R⁹ independently of one another are hydrogen, OH or a substituent from the group $C_1$–$C_{12}$alkyl, $C_2$–$C_{12}$alkenyl, $C_3$–$C_{12}$cycloalkyl, $C_3$–$C_{12}$cycloalkenyl, $C_2$–$C_{11}$heterocycloalkyl, $C_2$–$C_{11}$heterocycloalkenyl, $C_5$–$C_{10}$aryl, $C_1$–$C_9$heteroaryl, $C_6$–$C_{16}$aralkyl, $C_6$–$C_{16}$aralkenyl with $C_2$–$C_6$alkenylene and $C_5$–$C_{10}$aryl, $C_6$–$C_{15}$heteroaralkyl, $C_6$–$C_{15}$heteroaralkenyl and di-$C_6$–$C_{10}$aryl-$C_1$–$C_6$alkyl.

Particularly preferred bridge groups are $C_1$–$C_8$alkylene and $C_7$–$C_{12}$aralkylene.

A preferred subgroup of the compounds (I) comprises compounds of the formulae Ia, Ib and Ic:

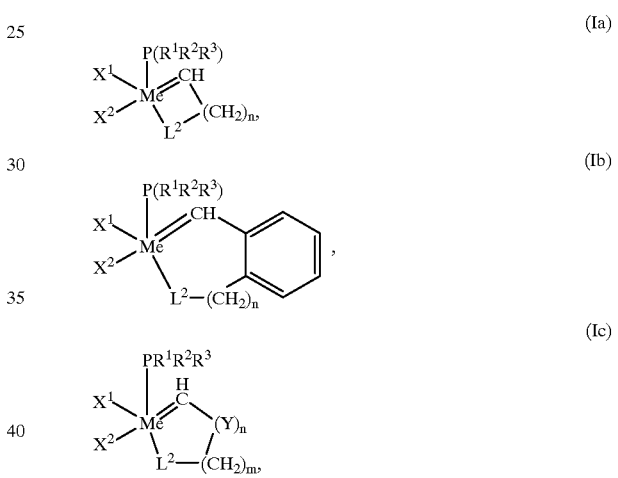

in which Me is ruthenium or osmium; X¹ and X² independently of one another are anionic ligands or X¹ and X² together are a bis-anionic ligand; Y is oxygen, sulfur or the group —R⁷N— or —PR⁷—, where R⁷ is hydrogen or a substituent from the group $C_1$–$C_6$alkyl, $C_6$–$C_{13}$aralkyl, sulfonyl and —C(=O)R$^{s2}$ and R$^{s2}$ is hydrogen or a substituent from the group $C_1$–$C_{12}$alkyl, $C_2$–$C_{12}$alkenyl, $C_3$–$C_{12}$cycloalkyl, $C_3$–$C_{12}$cycloalkenyl, $C_2$–$C_{11}$heterocycloalkyl, $C_2$–$C_{12}$heterocycloalkenyl, $C_5$–$C_{12}$aryl, $C_1$–$C_9$heteroaryl, $C_6$–$C_{14}$aralkyl, $C_2$–$C_{12}$heteroaralkyl, $C_5$–$C_{14}$aralkenyl or $C_2$–$C_{12}$heteroaralkenyl; n is 0 or 1; m is 0, 1, 2 or 3; and L² is an e⁻ donor ligand which is coordinated to the metal atom and is attached via the bridge group C* to the carbon atom of the carbene group and Y, and isomers of these compounds.

A particularly preferred embodiment of the invention relates to catalysts (I) whose preparation is depicted in the Examples.

The present invention additionally provides a process for preparing compounds of the formula I in which Me, X¹, X², Y, n, L¹ and L² are as defined above which comprises reacting, for example, a compound of the formula

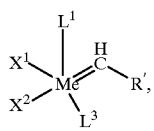

(II)

in which $X^1$, $X^2$ and $L^1$ are as defined under formula (I); R' is a substituent from the group $C_1-C_{20}$alkyl, $C_3-C_{12}$cycloalkyl, $C_2-C_{11}$heterocycloalkyl, $C_5-C_{12}$aryl, $C_1-C_9$heteroaryl and $_6-C_{14}$aralkyl, where alkyl, cycloalkyl, heterocycloalkyl, aryl, heteroaryl and aralkyl are unsubstituted or substituted by one or more substituents from the group $C_1-C_6$alkyl, $C_1-C_6$alkoxy, $C_1-C_6$haloalkyl, $C_5-C_{12}$aryl, $-NO_2$, $SO_3^-$, ammonium and halogen; and $L^3$ is a neutral $e^-$ donor ligand, with a compound:

(III)

in which $L^2$, $C^*$, Y and n are as defined above.

In a compound (III) the neutral $e^-$ donor ligand $L^3$ is as defined for $L^1$. The process is conducted in a manner known per se by dissolving the compound (II) in a solvent and subsequently adding the desired compound (III). The molar mass ratio of a compound (II) to the compound (III) is generally in the range from 1:1 to 1:100, preference being given to a ratio in the range from 1:1 to 1:5. The reaction takes place, for example, at a temperature in the range from −78° C. to 150° C., preferably from 0° C. to 100° C. and, with particular preference, at from room temperature to 50° C.

The invention likewise provides a composition comprising (α) dicyclopentadiene or another strained cycloolefin, or dicyclopentadiene in a mixture with another strained cycloolefin, and (β) a catalytic amount of at least one compound of the formula I, in which Me, $X^1$, $X^2$, Y, n, $L^1$ and $L^2$ are as defined, and isomers of these compounds and, if desired, further additives for polymers.

Dicyclopentadiene is the dimer of cyclopentadiene, which is known and commercially available and has the formula

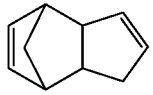

It is known that, together with further cyclopentadiene, dicyclopentadiene forms so-called Diels-Alder adducts and hence forms oligomers which can likewise be used. In accordance with the invention the composition may comprise pure dicyclopentadiene, oligomers of dicyclopentadiene or mixtures thereof. The oligomers are of the formula

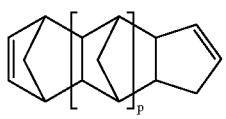

in which p is from 1 to 100, preferably from to 50, with particular preference from 1 to 20 and, with especial preference, from 1 to 10.

The cycloolefins known as strained cycloolefins, which may be present as comonomers in the composition of the invention, are known.

The cyclic olefins can be monocyclic or polycyclic, fused and/or bridged ring systems, which have, for example, from two to four rings and which are unsubstituted or substituted and can contain heteroatoms such as O, S, N or Si, for example, in one or more rings and/or can contain fused aromatic or heteroaromatic rings, such as o-phenylene, o-naphthylene, o-pyridinylene or o-pyrimidinylene. The individual cyclic rings include 3 to 16, preferably 3 to 12 and, with particular preference, 3 to 8 ring members. The cyclic olefins may contain further nonaromatic double bonds, preferably from 2 to 4 such additional double bonds depending on ring size. The ring substituents involved are those which are inert; in other words, those which do not impair the chemical stability of the ruthenium and osmium compounds. The cycloolefins are strained rings or ring systems.

If the cyclic olefins contain more than one double bond, for example 2 to 4 double bonds, then depending on the reaction conditions, on the chosen monomer and on the amount of catalyst it is also possible for crosslinked polymers to form.

Fused-on alicyclic rings contain preferably 3 to 8, more preferably 4 to 7 and, with particular preference, 5 or 6 ring carbon atoms.

The cyclic olefins which are present in the composition and which may be polymerized with the aid of the catalysts of the invention are known and are described, for example, in WO 96120235.

The comonomeric cycloolefins can be present in an amount of from 0.01 to 99% by weight, preferably from 0.1 to 95% by weight, with particular preference from 1 to 90% by weight and, with especial preference, from 5 to 80% by weight, based on the monomers present in the composition. Very particular preference is given to norbornene as comonomer in amounts, for example, of from 20 to 60% by weight.

The dienes which are present in the composition and which can be ring-closed with the aid of the catalysts of the invention are described, for example, in Miller et al. [Miller, S. J., Blackwell, H. E., Grubbs, R. H., *J. Am. Chem. Soc.* 118:9606–9614 (1996)] or in Grubbs et al. [Grubbs, R. H., Miller, S. J., Fu, G. C., *Acc. Chem. Res.* 28:446–452 (1995)].

The catalysts of the invention can also be used for breaking down unsaturated polymers or for isomerizing double bonds, as has already been described for ruthenium catalysts in McGrath and Grubbs [McGrath, D. V., Grubbs, R. H., *Organometallics* 13:224 (1994)].

The composition of the invention can comprise inert solvents. One particular advantage is that in the case of liquid monomers metathesis polymerization can be carried out without the use of a solvent. A further advantage is that the polymerization can even be carried out in water, polar and protic solvents or water/solvent mixtures. In such cases it is of advantage, in the context of the present invention, to use a surfactant.

Examples of suitable inert solvents are protic polar and aprotic solvents, which can be used alone or in mixtures of at least two solvents. Examples are ethers (dibutyl ether, tetrahydrofuran, dioxane, ethylene glycol monomethyl or dimethyl ether, ethylene glycol monoethyl or diethyl ether, diethylene glycol diethyl ether, triethylene glycol dimethyl ether), halogenated hydrocarbons, etc..

Compositions of the invention comprising a DCPD are insensitive to oxygen and moisture, which permits storage and reaction without an inert gas.

In the context of the present invention, catalytic amounts denote preferably an amount from 0.001 to 20 mol-%, with particular preference from 0.01 to 15 mol-% and, with very particular preference, from 0.01 to 10 mol-%, based on the amount of monomer. On the basis of the high thermocatalytic activity, very particular preference is given to amounts from 0.001 to 2 mol-%.

The composition of the invention which is used for the polymerization can be prepared directly prior to polymerization or can be used as a preformulated mixture, since the catalysts used are of particularly high stability. The mixture may even be stored for a prolonged period prior to polymerization, as a ready-to-use formulation, which is of advantage for large⁻ scale industrial use.

The composition of the invention can comprise additives suitable for polymers, which additives are preferably used as formulating auxiliaries to improve the chemical and physical properties. The auxiliaries can be present in surprisingly high proportions without adversely affecting the polymerization; for example, in amounts of up to 70% by weight, preferably from 1 to 70% by weight, more preferably from 5 to 60% by weight, with particular preference from 10 to 50% by weight and with especial preference from 10 to 40% by weight, based on the composition. Such auxiliaries have been disclosed in large numbers and are set out by way of example in the following list of auxiliaries:

1. Antioxidants
1. 1. Alkylated monophenols, for example 2,6-di-tert-butyl-4-methylphenol, 2-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, linear or sidechain-branched nonylphenols; such as 2,6-dinonyl- 4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.
1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-didodecyl-thiomethyl-4-nonylphenol.
1.3. Hydroquinones and alkylated hydroquinones, for example 2,6-di-tert-butyl-4-methoxyphenol, 2,5di-tert-butylhydroquinone, 2,5-di-tert-amylhydroquinone, 2,6-diphenyl-4-octadecyloxyphenol, 2,6di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl)adipate.
1.4. Tocopherols, for example α-tocopherol, β-tocopherol, γ-tocopherol, δ-tocopherol and mixtures thereof (vitamin E).
1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6di-sec-amylphenol), 4,4'-bis(2,6-dimethyl-4-hydroxyphenyl)disulfide.
1.6. Alkylidenebisphenols, for example 2,2'-methylenebis(6tert-butyl-4-methylphenol), 2,2'-methylenebis(6-tert-butyl-4-ethylphenol), 2,2'-methylenebis[4-methyl-6-(α-methylcyclo-hexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)dicyclopentadiene, bis[2-(3'-tert-butyl-2'-hydroxy-5'-methylbenzyl)-6tert-butyl-4-methylphenyl]terephthalate, 1,1-bis(3,5-dimethyl-2-hydroxyphenyl)butane, 2,2-bis(3,5di-tert-butyl-4-hydroxyphenyl)propane, 2,2-bis(5-tert-butyl-4-hydroxy-2-methylphenyl)-4-n-dodecylmercaptobutane, 1,1,5,5-tetra-(5-tert-butyl-4-hydroxy-2-methyphenyl)pentane.
1.7. O—, N— and S-benzyl compounds, for example 3,5, 3',5'-tetra-tert-butyl-4,4'-dihydroxydibenzyl ether, octadecyl 4hydroxy-3,5-dimethylbenzylmercaptoacetate, tridecyl 4-hydroxy-3,5-di-tert-butylbenzyimercaptoacetate, tris(3,5-di-tert-butyl-4-hydroxybenzyl)-amine, bis(4-tert-butyl-3-hydroxy-2,6-dimethylbenzyl) dithioterephthalate, bis(3,5-di-tert-butyl-4-hydroxybenzyl)sulfide, isooctyl 3,5-di-tert-butyl-4-hydroxybenzylmercaptoacetate.
1.8. Hydroxybenzlated malonates, for example dioctadecyl 2,2-bis(3,5-di-tert-butyl-2-hydroxybenzyl)malonate, dioctadecyl 2-(3-tert-butyl-4-hydroxy-5-methylbenzylmalonate, didodecyl mercaptoethyl-2,2-bis (3,5-di-tert-butyl-4-hydroxybenzyl)malonate, di-[4-(1,1,3,3-tetramethylbutyl)phenyl] 2,2-bis(3,5-di-tert-butyl-4-hydroxybenzyl)malonate.
1.9. Aromatic hydroxybenzyl compounds, for example 1,3, 5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3, 5-di-tert-butyl-4-hydroxybenzyl)phenol.
1.10. Triazine compounds, for example 2,4-bisoctylmercapto-6-(3,5-di-tert-butyl-4-hydroxyanilino)-1,3,5-triazine, 2-octylmercapto-4,6-bis(3, 5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3, 5-tris(3,5-di-tert-butyl-4-hydroxybenzyl) isocyanurate, 1,3,5-tris(4-tert-butyl-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)hexahydro-1,3,5-triazine, 1,3,5-tris(3,5-dicyclohexyl-4-hydroxybenzyl) isocyanurate.
1.11. Benzylphosphonates, for example dimethyl 2,5-di-tert-butyl-4-hydroxybenzyl-phosphonate, diethyl 3,5-di-tert-butyl-4-hydroxybenzylphosphonate, dioctadecyl 3,5-di-tert-butyl-4-hydroxybenzylphosphonate, dioctadecyl 5-tert-butyl-4hydroxy-3-methylbenzylphosphonate, the calcium salt of the monoethyl ester of 3,5-di-tert-butyl-4-hydroxybenzylphosphonic acid.
1.12. Acylaminophenols, for example 4-hydroxylauranilide, ⁴-hydroxystearanilide, octyl N-(3,5-di-tert-butyl-4-hydroxyphenyl)carbamate.
1.13. Esters of β-(3,5-di-tert-butyl-4-hydroxyphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)

oxalamide, 3-thiaundecanol, 3-thiapentadecanol, trimethylhexanediol, trimethylolpropane, 4-hydroxymethyl-1-phospha-2,6,7-trioxabicyclo[2.2.2] octane.

1.14. Esters of β-(5-tert-butyl-4-hydroxy-3-methyphenyl) propionic acid with mono- or polyhydric alcohols, e.g. with methanol, ethanol, n-octanol, i-octanol, octadecanol, 1,6-hexanediol, 1,9nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxalamide, 3-thiaundecanol, 3-thiapentadecanol, trimethylhexanediol, trimethylolpropane, 4-hydroxymethyl-1-phospha-2,6,7-trioxabicyclo[2.2.2] octane.

1.15. Esters of β-(3,5-dicyclohexyl-4-hydroxyphenl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl)isocyanurate, N,N'-bis(hydroxyethyl)-oxalamide, 3-thiaundecanol, 3-thiapentadecanol, trimethylhexanediol, trimethylolpropane, 4-hydroxymethyl-1-phospha-2,6,7-trioxabicyclo[2.2.2] octane.

1.16. Esters of 3,5-di-tert-butyl-4hydroxyphenylacetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)-oxalamide, 3-thiaundecanol, 3-thiapentadecanol, trimethyihexanediol, trimethylolpropane, 4-hydroxymethyl-1-phospha-2,6,7-trioxabicyclo[2.2.2] octane.

1.17. Amides of β-(3.5-di-tert-butyl-4-hydroxyphenyl) propionic acid, e.g. N,N'-bis(3,5-di-tert-butyl-4-hydroxyphenylpropionyl)hexamethylenediamide, N N'-bis(3,5-di-tert-butyl- 4-hydroxyphenylpropionyl) trimethylenediamide, N,N'-bis(3,5-di-tert-butyl-4-hydroxyphenyl-propionyl)hydrazide, N,N'-bis[2-(3-[3,5-di-tert-butyl-4-hydroxyphenyl]propionyloxy)ethyl]-oxamide (Naugard® XL-1 from Uniroyal).

1.18. Ascorbic acid (vitamin C).

1.19. Aminic antioxidants, for example N,N'-diisopropyl-p-phenylenediamine, N,N'-di-sec-butyl-p-phenylenediamine, N,N'-bis(1,4-dimethyl-pentyl)-p-phenylenediamine, N,N'-bis(1-ethyl-3-methyl-pentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-di-(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfonamido)-diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, di-(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diamino-diphenylmethane, 1,2-di[(2-methylphenyl)amino]ethane, 1,2-di (phenylamino)-propane, (o-tolyl)biguanide, di-[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyl-diphenylamines, mixtures of mono- and dialkylated tert-butyldiphenylamines, 2,3-dihydro-3,3-dimethyl-4H-1,4-benzothiazine, phenothiazine, a mixture of mono- and dialkylated tert-butyl/tert-octyl-phenothiazines, a mixture of mono- and dialkylated tert-octyl-phenothiazines, N-allylphenothiazine, N, N N',N'-tetraphenyl-1,4-diaminobut-2-ene, N,N-bis(2,2,6,6-tetramethylpiperidin-4-yl)hexamethylenediamine, bis(2,2,6,6-tetramethylpiperidin-4-yl)sebacate, 2,2,6,6-tetramethylpiperidin-4-one and 2,2,6,6-tetramethylpiperidin-4-ol.

2. UV Absorbers and Light Stabilizers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)-benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octoxyphenyl)benzotriazole, 2-(3',5'-di-tert-amyl-2'-hydroxyphenyl)benzotriazole, 2-(3',5'-bis(α,α-dimethylbenzyl)-2'-hydroxyphenyl)-benzotriazole, 2-(3'-tert-butyl-2'-hydroxy-5'-(2-octyloxycarbonylethyl) phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl) phenyl)-benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2isooctyloxycarbonylethyl) phenylbenzotriazole, 2,2'-methylenebis[4-(1,1,3,3-tetramethylbutyl)-6-benzotriazol-2-ylphenol]; the transesterification product of 2-[3'-tert-butyl-5'-(2-methoxy-carbonylethyl)-2'-hydroxyphenyl]benzotriazole with polyethylene glycol 300;

[R—CH$_2$CH$_2$—COO—CH$_2$CH$_2$]$_2$ $_{where\ R=}$3'-tert-butyl-4'-hydroxy-5'-2H-benzotriazol-2-yl-phenyl; 2-[2'-hydroxy-3'-(α,α-dimethylbenzyl)-5'-(1,1,3,3-tetramethylbutyl)phenyl]benzotriazole; 2-[2'-hydroxy-3'-(1,1,3,3-tetramethylbutyl)-5'-(α,α-dimethylbenzyl) phenyl]-benzotriazole.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivative.

2.3. Esters of substituted or unsubstituted benzoic acids, for example 4-tert-butyl-phenyl salicylate, phenyl salicylate, octylphenyl salicylate, dibenzoylresorcinol, bis(4-tert-butylbenzoyl)resorcinol, benzoylresorcinol, 2,4-di-tertbutylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-,ββ-diphenylacrylate or isooctyl α-cyano-β,β-diphenylacrylate, methyl α-carbomethoxycinnamate, methyl α-cyano-β-methyl-p-methoxy-cinnamate or butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thiobis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of monoalkyl esters, such as of the methyl or ethyl ester, of 4-hydroxy-3,5-di-tert-butylbenzylphosphonic acid, nickel complexes of ketoximes, e.g. of 2-hydroxy-4-methylphenyl undecyl ketoxime, nickel complexes of 1-phenyl-4-lauroyl-5-hydroxypyrazole, with or without additional ligands.

2.6. Sterically hindered amines, for example bis(2,2,6,6-tetramethylpiperidin-4-yl)sebacate, bis(2,2,6,6-tetramethylpiperidin-4-yl)succinate, bis(1 ,2,2,6,6-pentamethylpiperidin-4-yl) sebacate, bis(1-octyloxy-2,2,6,6-tetramethylpiperidin-4-yl)sebacate, bis(1,2,2,6,6-pentamethylpiperidyl)n-butyl-3,5-di-tert-butyl-4-hydroxybenzylmalonate, the condensate of 1-hydroxyethyl-2,2,6,6-tetramethyl-4-hydroxypiperidine and succinic acid, the linear or cyclic condensates of N,N'-bis(2,2,6,6-tetramethyl-4-piperidyl) hexamethylenediamine and 4-tert-octylamino-2,6-dichloro-1,3,5-s-triazine, tris(2,2,6,6-tetramethyl-4-piperidyl)nitrilotriacetate, tetrakis(2,2,6,6-tetramethyl-4-piperidyl) 1,2,3,4-butanetetraoate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis(1-octyloxy-2,2,6,6-tetramethylpiperidyl)sebacate, bis(1-octyloxy-2,2,6,6tetramethylpiperidyl)succinate, the linear or cyclic condensates of N,N'-bis-(2,2,6,6-tetramethyl-4-piperidyl)hexamethylenediamine and 4-morpholino-2,6-dichloro-1,3,5-triazine, the condensate of 2-chloro-4,6-di(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl) pyrrolidine-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, the condensate of N,N'-bis(2,2,6,6-tetramethyl-4-piperidyl)-hexamethylenediamine and 4-cyclohexylamino-2,6-dichloro-1,3,5-triazine, the condensate of 1,2-bis(3-aminopropylamino)ethane and 2,4,6-trichloro-1,3,5-triazine and also 4-butylamino-2,2,6,6-tetramethylpiperidine (CAS Reg. No. [136504-96-6]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxospiro[4.5]decane, the reaction product of 7,7,9,9-tetramethyl-2-cycloundecyl-1-oxa-3,8-diaza-4-oxospiro[4.5]decane and epichlorohydrine, 1,1-bis(1,2,2,6,6-pentamethyl-4-piperidyloxycarbonyl)-2-(4-methoxyphenyl)ether, N,N'-bisformyl-N,N'-bis(2,2,6,6-tetramethyl-4-piperidyl)-hexamethylenediamine, the diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, the reaction product of maleic anhydride-α-olefin copolymer and 2,2,6,6-tetramethyl-4-aminopiperidine or 1,2,2,6,6-pentamethyl-4-aminopiperidine.

2.7. Oxalamides, for example 4,4'-dioctyloxyoxanilide, 2,2'-diethoxy-oxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N+-bis(3-dimethylaminopropyl)oxalamide, 2-ethoxy-5-tert-butyl-2'-ethyloxanilide and its mixture with 2-ethoxy-2'-ethyl-5,4'-di-tert-butyloxanilide and mixtures of o- and p-methoxy- and of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropyloxy)phenyl]-4,6-bis(2,4-dimethylphenyl)-1,3,5-triazine, 2-[2-hydroxy-4-(2-hydroxy-3-octyloxypropyloxy)-phenyl]-4,6-bis(2,4-dimethylphenyl)-1,3,5-triazine, 2-[4-(dodecyloxy/tridecyloxy-2-hydroxypropoxy)-2-hydroxyphenyl]4,6-bis(2,4-dimethylphenyl)-1,3,5-triazine, 2-[2-hydroxy-4-(2-hydroxy-3-dodecyloxy-propoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy) phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1 3, 5-triazine.

3. Metal deactivators, for example, N,N'-diphenyloxalamide, N-salicylal-N'-salicyloyl hydrazine, N,N'-bis(salicyloyl)hydrazine, N,N'-bis(3,5-di-tert-butyl-4-hydroxyphenyl-propionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl) oxalyl dihydrazide, N,N'-bis(salicyloyl)thiopropionyl dihydrazide.

4. Phosphites, phosphines and phosphonites, for example triphenyl phosphite, diphenyl alkyl phosphites, phenyl dialkyl phosphites, tris(nonylphenyl)phosphite, trilauryl phosphite, trioctadecyl phosphite, trimethylphosphine, tri-n-butylphosphine, triphenylphosphine, distearyl pentaerythritol diphosphite, tris(2,4-di-tert-butylphenyl)phosphite, diisodecyl pentaerythritol diphosphite, bis(2,4-di-tert-butylphenyl)pentaerythritol diphosphite, bis(2,6-di-tert-butyl-4-methylphenyl)pentaerythritol diphosphite, bisisodecyloxypentaerythritol diphosphite, bis(2,4-di-tertbutyl-6-methylphenyl)pentaerythritol diphosphite, bis(2,4,6-tri-tert-butylphenyl)pentaerythritol diphosphite, tristearyl sorbitol triphosphite, tetrakis(2,4-di-tert-butylphenyl) 4,4′-biphenylene diphosphonite, 6-isooctyloxy-2,4, 8,10-tetra-tert-butyl-12H-dibenzo[d,g]-1,3,2-dioxaphosphocin, 6-fluoro-2,4,8,10-tetra-tert-butyl-12-methyl-dibenzo[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 2,2′,2″-nitrilo[triethyl-tris(3,3′,5,5″tetra-tert-butyl-1,1′-biphenyl-2,2′-diyl)phosphite], 2-ethylhexyl (3,3′,5,5′-tetra-tert-butyl-1,1′-biphenyl-2,2′-diyl)phosphite.

Particular preference is given to using the following phosphites:

Tris(2,4-di-tert-butylphenyl)phosphite (Irgafos®168, Ciba-Geigy), tris(nonylphenyl)'phosphite,

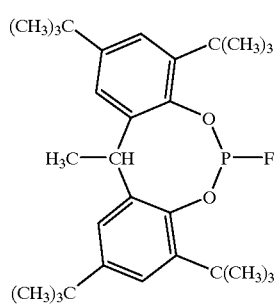
(A)

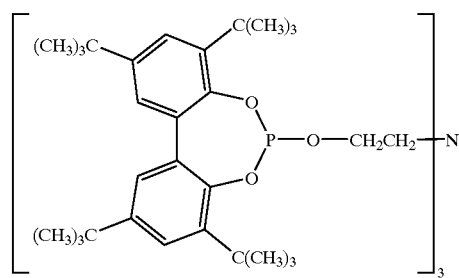
(B)

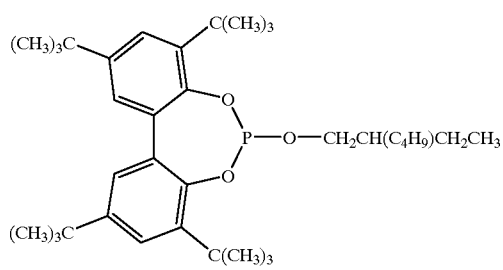
(C)

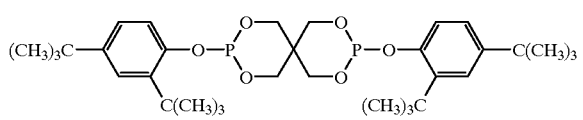
(D)

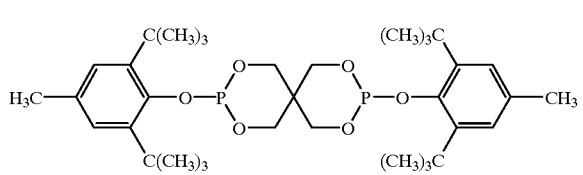
(E)

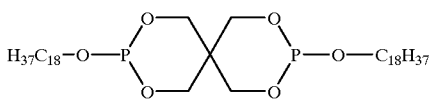
(F)

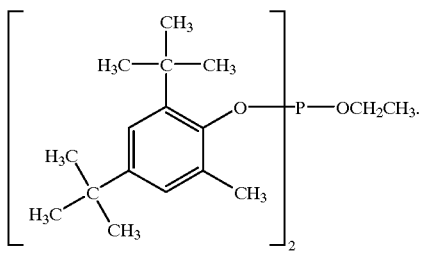
(G)

5. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine from hydrogenated tallow fatty amines.

6. Nitrones, for example N-benzyl alpha-phenyl nitrone, N-ethyl alpha-methyl nitrone, N-octyl alpha-heptyl nitrone, N-lauryl alpha-undecyl nitrone, N-tetradecyl alpha-tridecyl nitrone, N-hexadecyl alpha-pentadecyl nitrone, N-octadecyl alpha-heptadecyl nitrone, N-hexadecyl alpha-heptadecyl nitrone, N-octadecyl alpha-pentadecyl nitrone, N-heptadecyl alpha-heptadecyl nitrone, N-octadecyl alpha-hexadecyl-nitrone, and nitrones derived from N,N-dialkylhydroxylamines prepared from hydrogenated tallow fatty amines.

7. Thiosynergists, for example dilauryl thiodiproprionate or distearyl thiodipropionate.

8. Peroxide scavengers, for example esters of β-thiodipropionic acid, for example the lauryl, stearyl, myristyl or tridecyl esters, mercaptobenzimidazole, the zinc salt of 2-mercaptobenzimidazole, zinc dibutyldithiocarbamate, dioctadecyl disulfide, pentaerythritol tetrakis(β-dodecylmercapto)propionate.

9. Polyamide stabilizers, for example copper salts in combination with iodides and/or phosphorus compounds and salts of divalent manganese.

10. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate, potassium palmitate, antimony pyrocatecholate or zinc pyrocatecholate.

11. Nucleating agents, for example inorganic substances, such as talc, metal oxides such as titanium dioxide or magnesium oxide, phosphates, carbonates or sulfates of, preferably, alkaline earth metals; organic compounds such as mono- or polycarboxylic acids and their salts, such as 4-tert-butylbenzoic acid, adipic acid, diphenyl acetic acid, sodium succinate or sodium benzoate; and polymeric compounds, for example ionic copolymers (ionomers).

12. Filers and reinforcing agents, for example calcium carbonate, silicates, glass fibres, glass beads, talc, kaolin, mica, barium sulfate, metal oxides and hydroxides, carbon black, graphite, wood flour and flours or fibres of other natural products, and synthetic fibres.

13. Other additives, for example plasticizers, lubricants, emulsifiers, pigments, Theological additives, catalysts, levelling assistants, optical brighteners, flameproofing agents, antistatic agents, blowing agents.

14. Benzofuranones and indolinones, as described, for example, in U.S. Pat. Nos. 4,325,863; 4,338,244; 5,175,312, 5,216,052; 5,252,643; DE-A-4316611; DE-A-4316622; DE-A-4316876; EP-A-0589839 or EP-A-0591102, or 3-[4-(2-acetoxyethoxy)phenyl]-5,7-di-tert-butylbenzofuran-2-one, 5,7-di-tert-butyl-3-[4-(2-stearoyloxyethoxy)phenyl] benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3, 5-dimethylphenyl)-5,7-di-tert-butylbenzofuran-2-one, 3-(3, 5-dimethyl-4-pivaloyloxyphenyl)-5,7-di-tert-butylbenzofuran-2-one, 3-(3,4-dimethylphenyl)-5,7-di-tert-butylbenzofuran-2-one, 3-(2,3-dimethylphenyl)-5,7-di-tert-butylbenzofuran-2-one.

The invention provides, furthermore, a process for preparing metathesis polymers, which comprises heating a composition comprising (α') dicyclopentadiene or another strained cycloolefin, or dicyclopentadiene in a mixture with another strained cycloolefin, and (β') a catalytic amount of at least one compound of the formulae Ia–Ie, in which Me and Me independently of one another are ruthenium or osmium and X, X', Y, Y', $L^1$, $L^2$, $L^{2'}$, $L^3$, $L^{3'}$, $L^4$, $L^5$ and $L^{5'}$, Z, $Z^1$, $Z^{1'}$, R, R' and R" are as defined, and isomers of these compounds and, if desired, further additives for polymers and, if desired, subjecting the obtainable metathesis polymer to a shaping process.

The process of the invention is preferably carried out at a temperature of at least 0° C. In particular, the process of the invention is conducted at temperatures from 0° to 300° C., preferably at from room temperature to 250° C., with particular preference from room temperature to 200° C. and, with especial preference, at from room temperature to 160° C. Following polymerization it may be advantageous to condition the polymers at elevated temperatures, for example from 80 to 200° C. To prepare linear polymers the reaction is preferably carried out in dilute solutions.

Polymerization can be associated with shaping processes such as calendering, casting, compression moulding, injection moulding or extrusion, for example. With the process of the invention it is possible to produce materials for the machining production of shaped articles or thermoplastically deformable materials for producing mouldings of all kinds and coatings. Advantageously, shaping and polymerization are connected in solvent-free reactive systems, it being possible to employ processing techniques such as injection moulding, extrusion, polymerization in predetermined forms (possibly under superatmospheric pressure), for example.

The invention also provides the polymers obtainable by the process of the invention.

Of the polymers, preference is given to those containing only carbon and hydrogen.

The polymers prepared by the process of the invention can be homopolymers or copolymers with random distribution of the structural units, graft polymers or block polymers, and crosslinked polymers of this kind. They may have an average molecular weight ($\overline{Mw}$) of, for example, from 500 to 2 million daltons, preferably from 1000 to 1 million daltons (determined by GPC by comparison with polystyrene standards of narrow distribution).

It has surprisingly been found that the polymerization leads in high yields to a polydicyclopentadiene which corresponds to a linear polymer or copolymer having structural units of the formula

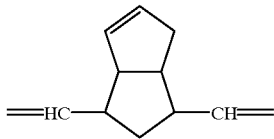

and represents a preferred subject of the invention. A further preferred subject of the invention comprises crosslinked copolymers having structural units of the formula

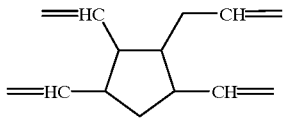

which can be prepared by the process of the invention.

The uncrosslinked or linear polymers comprise oligomers and polymers and can contain, for example, from 5 to 5000, advantageously from 10 to 2000, preferably from 20 to 1000, with particular preference from 20 to 500 and, with especial preference, from 20 to 300 structural units. Where the polymers are processed further preference is given to relatively low molecular weights, and in the case of processing to mouldings use is judiciously made of polymers having relatively high molecular weights.

Depending on the nature and amount of the monomers used, the polymers of the invention may have different properties. Some are notable for very high oxygen permeability, excellent dielectric properties (low dielectric constants, low loss factors or tan δ values), good thermal stability (glass transition temperatures above 100° C.), good toughnesses (impact and notched impact strength), flexibility and mechanical strengths (fracture resistance), hardness and low water absorption. Others have outstanding optical properties, such as high transparency and low reflective indices, for example. Also deserving of emphasis are the low shrinkage and the excellent surface properties (smoothness, gloss, adhesion). They can therefore be used in a very wide variety of industrial fields.

As coats on the surface of carrier materials, the polymers of the invention are notable for high adhesive strength. In addition, the coated materials are notable for high surface smoothness and gloss. Among the good mechanical properties particular emphasis should be placed on the low shrinkage and high impact strength, but also the thermal stability. Also deserving of mention are the ease of demoulding and the high solvent resistance. The surfaces can be modified further, for example painted or printed, and the high adhesive strengths of the coatings should be mentioned in this case, too.

The polymers obtainable in accordance with the invention are particularly suitable for producing articles of all kinds, such as mouldings for cars, boats, leisure articles, pallets, pipes, sheets, etc.; as insulating materials for producing electrical and electronic components; as implants; as binders for coating materials; as heat-curable compositions for modelling or as adhesives for bonding substrates having low surface energies (TEFLON, polyethylene or polypropylene). The compositions of the invention can also be used to prepare coatings by thermal polymerization, it being possible to use both clear (transparent) and even pigmented compositions. Both white and colour pigments can be used.

The production of mouldings by thermoplastic shaping processes for consumer articles of all kinds should also be mentioned.

The compositions of the invention are also suitable in particular for producing protective coats. The invention also provides a variant of the process of the invention for producing coated materials, in which the composition of the invention is applied with or without solvent as a film to a carrier, for example by dipping, brushing, flow coating, rolling, knife coating or spin coating techniques, the solvent (if used) is removed, and the film is heated for polymerization. With this process it is possible to modify or protect the surfaces of substrates (corrosion protection).

The present invention provides, furthermore, a coated carrier material wherein a coat of the polymer of the invention has been applied to a substrate.

The present invention likewise provides a coated substrate having a cured film of the polymer of the invention.

Examples of suitable substrates (carrier materials) are those of glass, minerals, ceramics, plastics, wood, semi-metals, metals, metal oxides and metal nitrides. The film thicknesses depend essentially on the desired use and can, for example, be from 0.1 to 1000 μm, preferably from 0.5 to 500 μm and, with particular preference, from 1 to 100 μm. The coated materials are notable for high adhesive strength and good thermal and mechanical properties.

The coated materials of the invention can be prepared by known methods such as brushing, knife coating, flow coating methods such as curtain coating or spin coating.

In the case of coatings, particularly good results are often achieved if the thermal metathesis polymerization is carried out with the additional use of cycloolefins which in addition contain from 1 to three, and preferably one, further double bonds and which in the context of the invention are polycyclic fused ring systems.

The examples which follow illustrate the invention.

A) PREPARING THE CATALYSTS

A1) Catalyst 1

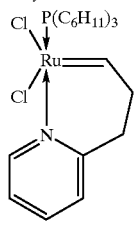
(1)

a) 200 mg of $RuCl_2P(C_6H_{11})_3(=CH-C_6H_5)$ are dissolved in 10 ml of methylene chloride. At

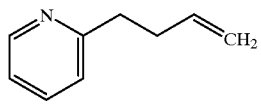
(1.1)

are added. After 30 minutes of stirring at RT the reaction mixture is concentrated in vacuo and the residue is washed with hexane ((3×5 ml) and dried in vacuo. The pure product (1) is obtained in virtually quantitative yield.

b) Alternatively to a) the compound (1) can be prepared by reacting a brown suspension containing 5.0 g (17.8 mmol) of $RuCl_2$(cis,cis-cyclooctadiene), 5.0 ml of triethylamine and 10.0 g of tricyclohexylphosphine in 250 ml of isopropanol. The suspension is stirred for 1 hour at 80° C. The clear red solution obtainable is cooled for one hour at −20° C. Following the addition of 35.6 ml of 1-molar HCl solution in diethyl ether, stirring is continued for 15 minutes. 4.1 ml of 1-hexyne are added to the yellow suspension, which is then stirred for two hours. The mixture is allowed to warm slowly to RT and then concentrated in vacuo. Following addition of 150 ml of methylene chloride and 4.7 g of 2-(3-butenyl)pyridine the mixture is stirred for two hours, then concentrated and washed with 3.25 ml of methanol. The fine, pale brownish powder is dried in vacuo.

$^1$H NMR: 19.46 (d, 1, $J_{PH}$=11.4 Hz, carbene-H);7.64, 7.23 (t, m, 3, Py-H); 3.65 (t, 2, γ-H); 2.5–1.2 (m, 35, β-H and $PCy_3$). $^{31}$P NMR: 36.8. Elemental analysis: C: 54.64 (calc.), 55.00 (found); H: 7.41 (calc.), 7.56 (found); N: 2.45 (calc.), 2.40 (found); Cl: 12.41 (calc.), 12.20 (found); P: 5.42 (calc.), 5.20 (found).

A2) Catalyst 2

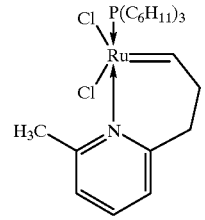
(2)

a) The pure product (2) is obtained in virtually quantitative yield from 200 mg of $RuCl_2(=CH-C_6H_5)P(C_6H_{11})_3$ and 5 equivalents of the compound (2.1)

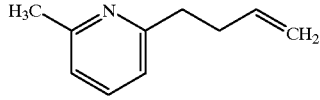
(2.1)

by the method of Example A1 a).

b) Following the method of Example A1 b) and reacting 5.0 g (17.8 mmol) of $RuCl_2$(cis,cis-cyclooctadiene), 5.0 ml of triethylamine and 10.0 g of tricyclohexylphosphine, and also 4.1 ml of 1-hexyne and 5.2 g of 2-(3-butenyl)-6-methylpyridine, gives the compound (2).

$^1$H NMR: 19.76 (dt, 1, $J_{PH}$=12.6 Hz, carbene-H); 7.50, 7.06 (t, m, 3, Py-H); 3.39 (t, 2, γ-H); 3.25 (s, 3, ortho-Me Py); 2.91 (m, 2, β-H); 2.4–1.2 (m, 33, $PCy_3$). $^{31}$P NMR: 34.7. Elemental analysis: C: 55.38 (calc.), 56.10 (found); H: 7.57 (calc.), 7.80 (found); N: 2.39 (calc.), 2.25 (found); Cl: 12.11 (calc.), 12.01 (found); P: 5.28 (calc.), 5.10 (found).

A3) Catalyst 3

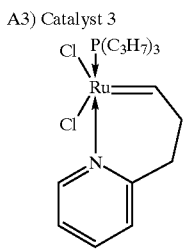

(3)

A5) Catalyst 5

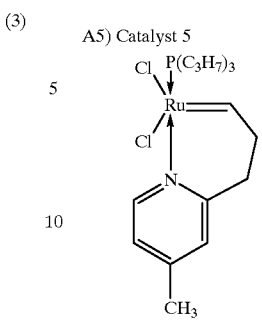

(5)

a) The pure product (3) is obtained in virtually quantitative yield from 200 mg of $RuCl_2(=CH—C_6H_5)P(C_3H_7)_3$ and 5 equivalents of compound (1.1) by the method of Example A1.

b) Following the method of Example A1 b) and reacting 5.0 g (17.8 mmol) of $RuCl_2$(cis,cis-cyclooctadiene), 5.0 ml of triethylamine and 7.2 ml of triisopropylphosphine, and also 4.1 ml of hexyne and 4.7 9 of 2-(3-butenyl)pyridine, gives the compound (3).

$^1$H NMR: 19.47 (dt, 1, $J_{PH}$=11.7 Hz, carbene-H); 7.51, 7.05 (t, m, 3, Py-H); 3.40 (t, 2, γ-H); 2.59 (m, 3, $PCHMe_2$); 2.50 (m, 2, β-H); 1.41 (dd, 18, $PCHMe_2$). $^{31}$P NMR: 44.1. Elemental analysis: C: 45.24 (calc.), 45.80 (found); H: 6.70 (calc.), 6.90 (found); N: 3.10 (calc.), 2.98 (found); Cl: 15.71 (calc.), 15.31 (found); P: 6.86 (calc.), 6.55 (found).

The pure product is obtained in virtually quantitative yield from 200 mg of $RuCl_2(=CH—C_6H_5)[P(C_3H_7)_3]_2$ and 2 equivalents of compound (5.1)

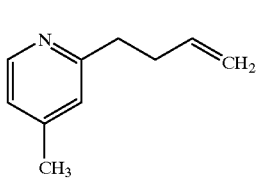

(5.1)

by the method of Example A1. $^1$H NMR: 19.7 (m, 1, carbene$^-$ H). $^{31}$P NMR: 40.

A4) Catalyst 4

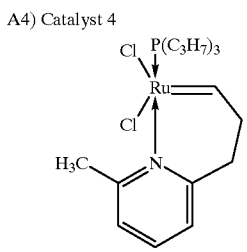

(4)

A6) Catalyst 6

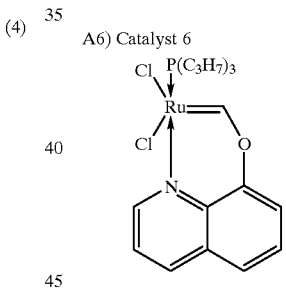

(6)

a) The pure product is obtained in virtually quantitative yield from 200 mg of $RuCl_2(=CH—C_6H_5)P(C_3H_7)_3$ and 5 equivalents of compound (2.1) by the method of Example A1.

b) Following the method of Example A1 b) and reacting 5.0 g (17.8 mmol) of $RuCl_2$(cis,cis-cyclooctadiene), 5.0 ml of triethylamine and 7.2 ml of triisopropylphosphine, and also 4.1 ml of hexyne and 5.2 g of 2-(3-butenyl)-6-methylpyridine, gives the compound (4).

$^1$H NMR: 19.78 (dt, 1, $J_{PH}$=13.1 Hz, carbene-H); 8.75 (d, 1, ortho-H Py); 7.65, 7.25 (t, m, 3, Py-H); 3.65 (t, 2, γ-H); 3.22 (s, 3, ortho-Me Py); 2.59 (m, 3, $PCHMe_2$); 2.93 (m, 2, β-H) (dd, 18, $PCHMe_2$). $^{31}$P NMR: 42.3. Elemental analysis: C: 46.45 (calc.), 46.95 (found); H: 6.93 (calc.), 7.05 (found); N: 3.01 (calc.), 2.90 (found); Cl: 15.24 (calc.), 15.35 (found); P: 6.66 (calc.), 6.50 (found).

The pure product is obtained in virtually quantitative yield from 200 mg of $RuCl_2(=CH—C_6H_5)[P(C_3H_7)_3]_2$ and 1.5 equivalents of compound (6.1)

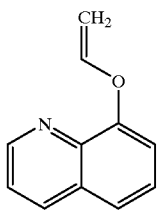

(6.1)

by the method of Example A1. $^1$H NMR: 15.46 (d, 1, $J_{PH}$=11.53 Hz, carbene-H); 9.0–7.4 (m, 6, quinoline-H); 2.69 (m, 3, $PCHMe_2$); 1.47 (m, 18, $PCHMe_2$). $^{31}$P NMR: 44.9.

B) EXAMPLES—POLYMERIZATIONS

B1) Polymerizing DCPD (dicyclopentadiene)

(94% from Shell, degassed) is admixed with 0.3% (by weight) of catalyst. Curing conditions: 1 h 80° C., 1h 100° C., 2 h 120° C. ΔH- and $T_g$ measurements by DSC (Differential Scanning Calorimetry), weight loss measurement by TGA (Thermogravimetric Analysis) to 300° C.

| Catalyst | Onset Temperature[a] | ΔH [J/g] | $T_g$ [° C.] | Weight loss [%] |
|---|---|---|---|---|
| 1 | 55 | 391 | 60 | 9.0 |
| 2 | <30 | n.d. | 86 | 2.4 |
| 3 | n.d. | 360 | 108 | 4.5 |
| 4 | n.d. | 380 | 136 | 3.4 |

[a]Temperature at which gelling begins.
n.d.: not determined b) DCPD (98%, from BFGoodrich) is admixed with catalyst ([DCPD]i[cat]=7500/1). Then DSC is used to measure the exotherm and the onset temperature. In a second round, the glass transition temperature of the polyDCPD is measured.

| Catalyst | Onset Temp. [° C.] | ΔH [J/g] | Tg [° C.] |
|---|---|---|---|
| 1 | 76 | 257 | 100 |
| 2 | 35 | 343 | 140 |
| 3 | 76 | 380 | 137 |
| 4 | 40 | 371 | 138 |
| 5 | 45 | 368 | 140 |

B2) Polymerizing dimethyl 2-norbornene-5,6-dicarboxylate

Dimethyl 2-norbornene-5,6-dicarboxylate is dissolved in $CH_2Cl_2$ (40%) and the solution is subsequently incubated at 20° C. in the presence of 3% by weight of catalyst 2. The polymer formed is precipitated with methanol. Mn and M, are determined by GPC (Gel Permeation Chromatography).

| Time [h] | Yield [%] | $M_n$ [× $10^3$] | $M_w/M_n$ |
|---|---|---|---|
| 1.5 | 22.5 | 25.3 | 1.99 |
| 4.5 | 46 | 28.8 | 2.12 |
| 8 | 50 | 30.4 | 2.02 |
| 24 | 72 | 23.9 | 2.06 |

B3) Polymerizing Norbornene 2 mg of catalyst 6 and 200 mg of norbornene (500 equivalents) are dissolved in 5 ml of chloroform. After 4 hours, the polymer is obtained in a yield of 92% by precipitation in methanol. The polymer contains 90% of trans double bonds.

B4) Ring-closure Reaction of Diethyl diallylmalonate

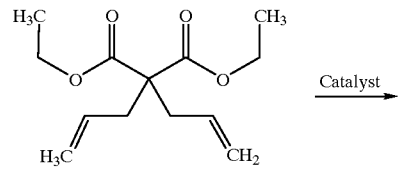

$\xrightarrow{\text{Catalyst}}$

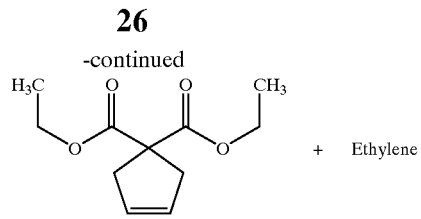 + Ethylene

The catalyst (0.5 mol % relative to open-chain diolefin) is added under nitrogen to a solution of 120 mg (0.5 mmol) of diethyl diallylmalonate in 2 ml of methylene chloride. The mixture is reacted with stirring at the stated temperatures and the conversion, i.e. the formation of the cyclic olefin, is monitored by means of GC at periodic intervals in time.

| Catalyst | Solvent | Temperature (° C.) | Time (h) | Conversion (%) |
|---|---|---|---|---|
| 3 | $CH_2Cl_2$ | RT | 24 | 5.5 |
| 3 | 1,1,2-Trichloroethane | 60 | 3 | 7.5 |
| 3 | 1,1,2-Trichloroethane | 60 | 5 | 9.6 |
| 3 | 1,1,2-Trichloroethane | 60 | 24 | 13 |
| 4 | 1,1,2-Trichloroethane | RT | 0.5 | 5 |
| 4 | 1,1,2-Trichloroethane | RT | 6 | 52 |
| 4 | 1,1,2-Trichloroethane | RT | 72 | 94 |
| 4 | 1,1,2-Trichloroethane | 60 | 0.5 | 70 |
| 4 | 1,1,2-Trichloroethane | 60 | 6 | 100 |

B5) Effect of Additives [Antioxidants, HALS (HALS:Hindered Amine Light Stabilizers), UV-Absorbers]

98%, BFGoodrich) is admixed with 0.03% by weight of the relevant catalyst—see the table—and with the relevant additive in the amount indicated in the table. Curing 2 hours at 120° C., 1 hour at 150° C. Determination of $T_g$ by DSC.

| Catalyst | Additive added | Additive content (% by wt.) in DCPD | $T_g$ |
|---|---|---|---|
| 3 | — | — | 142 |
| 4 | — | — | 140 |
| 3 | 1 | 1 | 140 |
| 3 | 2 | 1 | 140 |
| 3 | 3 | 1 | 141 |
| 3 | 4 | 1 | 139 |
| 3 | 1 | 2 | 140 |
| 3 | 1 | 5 | 139 |
| 4 | 1 | 1 | 140 |
| 4 | 2 | 1 | 139 |
| 4 | 3 | 1 | 139 |
| 4 | 4 | 1 | 140 |
| 4 | 1 | 2 | 139 |
| 4 | 1 | 5 | 139 |

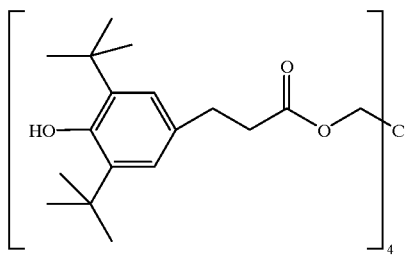

1 (IRGANOX 1010)

27

-continued

| Catalyst | Additive added | Additive content (% by wt.) in DCPD | $T_g$ |
|---|---|---|---|

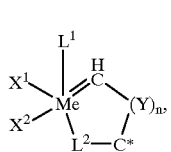

2 (HP-136)

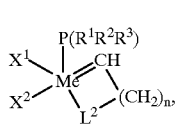

3 (TINUVIN 765)

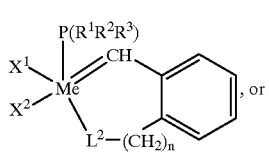

4 (TINUVIN 328)

b) Experimental conditions as in a). Additive mixtures are employed.

Additive mixture 1:
 0.75% by weight of 1 (IRGANOX 1010)
 0.25% by weight of 2 (IRGANOX HP 136)
 0.40% by weight of 3 (TINUVIN 765)

Additive mixture 2:
 0.75% by weight of 1 (IRGANOX 1010)
 0.25% by weight of 2 (IRGANOX HP 136)
 0.40% by weight of 3 (TINUVIN 765)
 0.20% by weight of 4 (TINUVIN 328)

| Catalyst | Additive added (mixture) | $T_g$ in ° C. |
|---|---|---|
| A | — | 142 |
| B | — | 140 |
| A | 1 | 140 |
| B | 1 | 141 |
| A | 2 | 142 |
| B | 2 | 139 |

What is claimed is:

1. A compound of the formula I

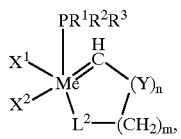

(I)

in which
Me is ruthenium or osmium;
$X^1$ and $X^2$ independently of one another are anionic ligands, or $X^1$ and $X^2$ together are a bis-anionic ligand;
Y is oxygen, sulfur or the groups —$NR^7$— or —$PR^7$—, where $R^7$ is hydrogen or a substituent selected from the group $C_1$–$C_6$alkyl, $C_6$–$C_{13}$aralkyl, sulfonyl and —C(=O)$R^{s2}$ and $R^{s2}$ is hydrogen or a substituent selected from the group $C_1$–$C_{12}$alkyl, $C_2$–$C_{12}$alkenyl, $C_3$–$C_{12}$cycloalkyl, $C_3$–$C_{12}$cycloalkenyl, $C_2$–$C_{11}$heterocycloalkyl, $C_2$–$C_{11}$heterocycloalkenyl, $C_5$–$C_{12}$aryl, $C_1$–$C_9$heteroaryl, $C_6$–$C_{14}$aralkyl, $C_2$–$C_{13}$heteroaralkyl, $C_6$–$C_{14}$aralkenyl and $C_3$–$C_{13}$heteroaralkenyl;
n is 0 or 1;
$L^1$ is tertiary phosphine;
and $L^2$ is a neutral e⁻ donor ligand which is coordinated to the metal atom and is attached via the bridge group C* to the carbon atom of the carbene group if n is 0 and to Y if n is 1.

2. A compound according to claim 1 of the formulae:

(Ia)

$$\begin{array}{c}X^1\\X^2\end{array}\!\!\!\!Me\!\!\!\!\begin{array}{c}P(R^1R^2R^3)\\CH\\L^2\end{array}\!\!\!\!(CH_2)_n,$$

(Ib)

$$\begin{array}{c}X^1\\X^2\end{array}\!\!\!\!Me\!\!\!\!\begin{array}{c}P(R^1R^2R^3)\\CH\\L^2-(CH_2)_n\end{array}, \text{ or}$$

(Ic)

$$\begin{array}{c}X^1\\X^2\end{array}\!\!\!\!Me\!\!\!\!\begin{array}{c}PR^1R^2R^3\\H\\C\\L^2-(CH_2)_m\end{array}\!\!\!\!(Y)_n,$$

in which
Me is ruthenium or osmium;
$R^1$, $R^2$ and $R^3$ independently of one another are $C_1$–$C_{12}$alkyl, $C_5$–$C_8$cycloalkyl, $C_6$–$C_{12}$aryl or $C_7$–$C_{13}$aralkyl in which alkyl, cycloalkyl, aryl and aralkyl are unsubstituted or substituted by one or more substituents selected from the group $C_1$–$C_6$alkyl, $C_1$–$C_6$alkoxy, $C_1$–$C_6$haloalkyl, sulfo, trimethylamino, triethylamino, ammonium and trifluoromethyl;
$X^1$ and $X^2$ independently of one another are anionic ligands or $X^1$ and $X^2$ together are a bis-anionic ligand;
Y is oxygen, sulfur or the group —$NR^7$— or —$PR^7$—, where $R^7$ is hydrogen or a substituent selected from the group $C_1$–$C_6$alkyl, $C_6$–$C_{13}$aralkyl, sulfonyl and —C(=O)$R^{s2}$ and $R^{s2}$ is hydrogen or a substituent selected from the group $C_1$–$C_{12}$alkyl, $C_2$–$C_{12}$alkenyl, $C_3$–$C_{12}$cycloalkyl, $C_3$–$C_{12}$cycloalkenyl, $C_2$–$C_{11}$heterocycloalkyl, $C_2$–$C_{11}$heterocycloalkenyl, $C_5$–$C_{12}$aryl, $C_1$–$C_9$heteroaryl, $C_6$–$C_{14}$aralkyl, $C_2$–$C_{12}$heteroaralkyl, $C_5$–$C_{14}$aralkenyl or $C_2$–$C_{12}$heteroaralkenyl;

n is 0 or 1;

m is 0, 1, 2 or 3;

and $L^2$ is a neutral $e^-$ donor ligand which is coordinated to the metal atom.

3. A compound according to claim 1 of the formula:

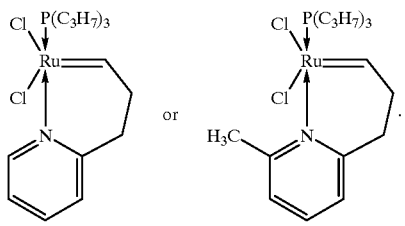

4. A process for preparing a compound of the formula I according to claim 1 in which Me, $X^1$, $X^2$, Y, n, $L^1$ and $L^2$ are as defined in claim 1 which comprises reacting a compound of the formula

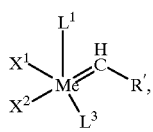

(II)

in which $X^1$, $X^2$ and $L^1$ are as defined under formula (I) in claim 1; R' is a substituent selected from the group $C_1$–$C_{20}$alkyl, $C_3$–$C_{12}$cycloalkyl, $C_2$–$C_{11}$heterocycloalkyl, $C_5$–$C_{12}$aryl, $C_1$–$C_9$heteroaryl and $C_6$–$C_{14}$aralkyl, where alkyl, cycloalkyl, heterocycloalkyl, aryl, heteroaryl and aralkyl are unsubstituted or substituted by one or more substituents selected from the group $C_1$–$C_6$alkyl, $C_1$–$C_6$alkoxy, $C_1$–$C_6$haloalkyl, $C_6$–$C_{16}$aryl, —$NO_2$, $SO_3^-$, ammonium and halogen; and $L^3$ is a neutral $e^-$ donor ligand; with a compound:

$$L^2C^*(Y)_n CHCH_2 \qquad (III)$$

in which $L^2$, $C^*$, Y and n are as defined above.

5. A composition comprising (α) dicyclopentadiene or another strained cycloolefin, or dicyclopentadiene in a mixture with another strained cycloolefin, and (β) a catalytic amount of at least one compound of the formula I according to claim 1 in which Me, $X^1$, $X^2$, Y, n, $L^1$ and $L^2$ are as defined in claim 1.

6. A process for preparing metathesis polymers, which comprises heating a composition comprising (α') dicyclopentadiene or another strained cycloolefin, or dicyclopentadiene in a mixture with another strained cycloolefin, and (β') a catalytic amount of at least one compound of the formula I according to claim 1 in which Me, $X^1$, $X^2$, Y, n, $L^1$ and $L^2$ are as defined in claim 1 and, optionally, further additives for polymers and, optionally, subjecting the obtainable metathesis polymer to a shaping process.

* * * * *